US008438049B2

(12) United States Patent  
Ranicar, III et al.

(10) Patent No.: US 8,438,049 B2  
(45) Date of Patent: May 7, 2013

(54) SYSTEM AND METHOD FOR PROCESSING DATA RELATED TO GROUP BENEFIT INSURANCE HAVING CRITICAL ILLNESS COVERAGE

(75) Inventors: James A. Ranicar, III, North Granby, CT (US); Stacie F. Windisch, Simsbury, CT (US)

(73) Assignee: Hartford Fire Insurance Company, Hartford, CT (US)

( * ) Notice: Subject to any disclaimer, the term of this patent is extended or adjusted under 35 U.S.C. 154(b) by 90 days.

(21) Appl. No.: 13/196,393

(22) Filed: Aug. 2, 2011

(65) Prior Publication Data

US 2013/0035962 A1 Feb. 7, 2013

(51) Int. Cl.
G06Q 40/00 (2012.01)

(52) U.S. Cl.
USPC .................................. 705/4; 705/1.1

(58) Field of Classification Search ........................ 705/4
See application file for complete search history.

(56) References Cited

U.S. PATENT DOCUMENTS

| | | | |
|---|---|---|---|
| 5,875,435 A | 2/1999 | Brown | |
| 5,909,673 A | 6/1999 | Gregory | |
| 5,926,800 A | 7/1999 | Baronowski et al. | |
| 6,181,814 B1 | 1/2001 | Carney | |
| 6,275,807 B1 | 8/2001 | Schirripa | |
| 6,401,079 B1 | 6/2002 | Kahn et al. | |
| 6,411,938 B1 | 6/2002 | Gates et al. | |
| 6,829,588 B1 | 12/2004 | Stoutenburg et al. | |
| 6,938,048 B1 | 8/2005 | Jilk et al. | |
| 7,050,932 B2 | 5/2006 | Selby et al. | |
| 7,110,979 B2 | 9/2006 | Tree | |
| 7,143,051 B1 | 11/2006 | Hanby et al. | |
| 7,194,426 B1 | 3/2007 | Box | |
| 7,213,064 B2 | 5/2007 | Smith et al. | |
| 7,229,013 B2 | 6/2007 | Ben-Aissa | |
| 7,249,073 B1 | 7/2007 | Lesk | |
| 7,260,548 B1 | 8/2007 | Allsup | |
| 7,324,950 B2 | 1/2008 | Sherman | |
| 7,343,310 B1 | 3/2008 | Stender | |
| 7,418,429 B1 | 8/2008 | Mok et al. | |
| 7,457,776 B1 | 11/2008 | Caruso et al. | |
| 2002/0022982 A1 | 2/2002 | Cooperstone et al. | |
| 2002/0069077 A1 | 6/2002 | Brophy et al. | |
| 2002/0103678 A1 | 8/2002 | Burkhalter et al. | |
| 2002/0103680 A1* | 8/2002 | Newman | 705/4 |

(Continued)

OTHER PUBLICATIONS

Policy Summary—UltraCare Plus Plan Jan. 1, 2010.*

(Continued)

Primary Examiner — William Rankins  
(74) Attorney, Agent, or Firm — Howard IP Law Group, PC

(57) ABSTRACT

A computer system for processing data related to a group benefit insurance policy issued to a group policyholder to extend coverage to individual insureds and having a critical illness benefit includes a data storage device storing data indicative of: a plurality of categories of medical diagnoses; a plurality of diagnoses associated with each of the categories; a first occurrence value; a second occurrence value; and prior claims under the critical illness benefit by the insured. The system is configured to provide instructions for payment of the first occurrence value for a first diagnosis of an insured in a category, and the second occurrence value, which is less than the first occurrence value, for a second diagnosis of the insured in the same category.

20 Claims, 9 Drawing Sheets

U.S. PATENT DOCUMENTS

| | | | |
|---|---|---|---|
| 2002/0138306 A1 | 9/2002 | Sabovich | |
| 2002/0184148 A1 | 12/2002 | Kahn et al. | |
| 2002/0188480 A1 | 12/2002 | Liebeskind et al. | |
| 2003/0171956 A1 | 9/2003 | Cox et al. | |
| 2003/0182147 A1 | 9/2003 | Mahoney et al. | |
| 2003/0187694 A1 | 10/2003 | Rowen | |
| 2003/0204421 A1 | 10/2003 | Houle et al. | |
| 2003/0225690 A1 | 12/2003 | Eaton | |
| 2003/0229522 A1 | 12/2003 | Thompson et al. | |
| 2004/0049397 A1 | 3/2004 | Leisure et al. | |
| 2004/0049436 A1 | 3/2004 | Brand et al. | |
| 2004/0158512 A1 | 8/2004 | Dean et al. | |
| 2004/0167853 A1 | 8/2004 | Sharma | |
| 2004/0267595 A1 | 12/2004 | Woodings et al. | |
| 2005/0055251 A1* | 3/2005 | Ashley et al. | 705/4 |
| 2005/0228728 A1 | 10/2005 | Stromquist | |
| 2005/0288971 A1 | 12/2005 | Cassandra | |
| 2006/0020545 A1 | 1/2006 | Lindheimer et al. | |
| 2006/0036528 A1 | 2/2006 | Harnsberger | |
| 2006/0064313 A1 | 3/2006 | Steinbarth et al. | |
| 2006/0100912 A1 | 5/2006 | Kumar et al. | |
| 2006/0173775 A1 | 8/2006 | Cullen, III et al. | |
| 2006/0212393 A1 | 9/2006 | Lindsay Brown | |
| 2006/0224475 A1 | 10/2006 | Kramer et al. | |
| 2006/0247953 A1 | 11/2006 | Pollack et al. | |
| 2006/0253306 A1 | 11/2006 | Richardson et al. | |
| 2006/0259437 A1 | 11/2006 | Armstrong et al. | |
| 2007/0136156 A1 | 6/2007 | Seeley et al. | |
| 2007/0185741 A1 | 8/2007 | Hebron et al. | |
| 2007/0185791 A1 | 8/2007 | Chan et al. | |
| 2007/0185793 A1 | 8/2007 | George | |
| 2007/0185797 A1 | 8/2007 | Robinson | |
| 2007/0203756 A1 | 8/2007 | Sears et al. | |
| 2008/0147447 A1 | 6/2008 | Roche et al. | |
| 2008/0162535 A1 | 7/2008 | Bak | |
| 2008/0167903 A1 | 7/2008 | Hall et al. | |
| 2008/0281641 A1 | 11/2008 | Pilzer et al. | |

OTHER PUBLICATIONS

The Hartford; Self Administered Billing Premium Statement (Document prepared for use by customers), at least as early as Jul. 8, 2008, 2 pages.

The Hartford; List Bill Premium Statement (Document prepared for use by customers), at least as early as Jul. 8, 2008, 4 pages.

The Hartford; Introducing Your Bill from . . . The Hartford (Document prepared for use by customers), at least as early as Jul. 8, 2008, 7 pages.

The Hartford; List Billing (Document prepared for use by customers), at least as early as Jul. 8, 2008, 18 pages.

The Hartford; Self-Administered Billing (Document prepared for use by customers), at least as early as Jul. 8, 2008, 28 pages.

The Hartford; List Billing—Recordkeeping; Table of Contents (Document prepared for use by customers), at least as early as Jul. 8, 2008, 12 pages.

Barbara Whitaker; "A Less Burdensome Path to Safeguard the Future"; The New York Times (Aug. 3, 1997), 3 pages.

Fort Dearborn Life; "Benefits Manager Overview and Billing Methods" (2007), 2 pages.

Gerald M. Groe, PhD et al.; "Research Update: Information Technology and HR"; Human Resources Planning; 91:1(1996), p. 56; 6 pages.

Al Wright; "Tools for Automating Complex Compensation Programs", Compensation and Benefits Review; Nov./Dec. 2003, 9 pages.

"The Hartford Partners with Time+Plus to Reach More Small Businesses", PR Newswire. New York: Mar 30, 2004. p. 1, 2 pages.

"Paychex Teams Up With the Hartford to Help Small Businesses Manage Workers' Compensation Costs", Business Editors. Business Wire. New York:Jun. 15, 1999, p. 1, 2 pages.

Jacquelyn Lynn; "Pay As You Go"; Entrepreneur, Apr. 2001, 2 pages.

"Carrier and Payroll Service Bypass Agents Pay-as-you-go system nets 10,000 clients in a year", SBB. Small Business Banker. New York: Oct 2000. vol. 1, Iss. 9; p. 11, 2 pages.

Emma Thelwell; "How to protect yourself if illness strikes"; Oct. 14, 2006; The Daily Telegraph; p. 5, 3 pages.

Faith Archer, "A long spell off work can wreck your finances", Apr. 15, 2006, The Daily Telegraph, p. 5, 3 pages.

Richard Dyson, "The mother who refused to give up", Mar. 19, 2006, Mail on Sunday, p. 13, 3 pages.

unknown, "CIGNA Introduces Insurance for Coping with Critical Illness", Apr. 29, 1998, PRNewswire, p. 1, 4 pages.

Roger J. Stalowicz, "Critical Illness Life Insurance : Innovation to address a need", Sep. 1998, Journal of the American Society of CLU & ChFC, vol. 52, Issue 5, p. 54, 8 pages.

Harvey W. Rubin, Dictionary of Insurance Terms, 2000, Barron's Educational Series, Inc., Fourth Edition, pp. 136-137.

"Could your bank account survive a serious illness"; Unum Life insurance Company of America; Portland, ME; Nov. 2009; 2 pages.

Sternberg, Erich; "Critical Illness: Delivering a Benefit to Financial Health"; www.voluntarybenefitsmagazine.com; Nov. 5, 2010, 2 pages.

Warren S. Hersch, "Weighing the Merits of Settlement Options", Nov. 14, 2005, National Underwriter Life & Health, vol. 109, Issue 43, p. 68, pp. 1-2.

Unknown, "Deduction of Long Term Care Expenses", Excerpts from I.R.S. Notice 97-31 re: Deduction of Long-Term Care Expenditures, NextSteps, http:www.lifemanagement.com/nsa7.1.1917/, May 27, 1997, pp. 1-2.

* cited by examiner

SYSTEM AND METHOD FOR PROCESSING DATA RELATED TO GROUP BENEFIT INSURANCE HAVING CRITICAL ILLNESS COVERAGE

FIELD OF INVENTION

The present invention relates to computer systems, and particularly to computer systems for use in the financial services field, and particularly for processing of data related to group benefit insurance.

BACKGROUND

In the insurance field, insurance coverage for individuals is generally offered and issued either on an individual basis to a named individual insured, or to a group of individuals. The group is typically a group of employees of an employer, but may include other types of groups such as associations, unions, clubs fraternal organizations and other types of groups.

Group benefit policies make various types of insurance coverage available to any individual in the group, generally with guaranteed issue or minimal underwriting. Various coverages including life, long-term disability, short-term disability, dental care, vision care and critical illness are often available. Critical illness benefits may provide that the insured is entitled to a lump sum payment upon diagnosis of a serious medical condition, such as certain cancers, heart attack, serious illnesses or conditions affecting other vital organs, and the like.

In many such policies, an individual may be permitted a single claim for critical illness benefits in a lifetime. From an underwriting perspective, there is a high risk of an individual who has been diagnosed with a critical illness being diagnosed with a second critical illness. For example, an individual who has had a heart attack is at much higher risk than the general population of a second heart attack or another serious condition affecting the heart or circulatory system. Accordingly, insurance companies tend not to offer coverage for a second claim, as there is likely to be little or no interest in purchasing coverage at appropriate premium levels given the risk.

Some insurance companies make recurrence benefits available. Thus, an insured who suffers a heart attack and receives a lump sum payment under the critical illness benefit may, upon suffering a second heart attack or receiving a diagnosis of cancer, after a suitable waiting period, be able to receive a second payment under the same policy. The second payment may be lower than the first payment, and may be the final payment available to the insured under the critical illness policy.

It is desirable to provide critical illness benefits in group benefit policies that provide an incentive for the insured to continue the policy after receiving a benefit, wile providing reasonable management of insurer risks.

SUMMARY

In an embodiment, a computer system for processing data related to a group benefit insurance policy issued to a group policyholder to extend coverage to individual insureds and having a critical illness benefit, includes: a data storage device storing data indicative of: a plurality of categories of medical diagnoses; a plurality of diagnoses associated with each of the categories; a first occurrence value; a second occurrence value; and prior claims under the critical illness benefit by the insured; and a processor in communication with the data storage device. The processor is configured to: receive via a network from a user-accessible device data associated with a current claim for a critical illness benefit, the data including data indicative of an insured and a diagnosis of a medical condition of the insured; access from the data storage device the data indicative of diagnoses, categories, and prior claims; determine a category corresponding the diagnosis of the current claim; determine whether a prior claim had been paid to the insured for a diagnosis in the determined category; responsive to determining that no prior claim had been paid to the insured for a diagnosis in the determined category, provide an output signal having data indicative of instructions to pay the insured the first occurrence value; and responsive to determining that one and only one prior claim had been paid to the insured for a diagnosis in the determined category, provide an output signal having data indicative of instructions to pay the insured the second occurrence value.

In an embodiment, a computer-implemented method for processing data related to a group benefit insurance policy issued to a group policyholder to extend coverage to individual insureds and having a critical illness benefit, includes: prompting a user at a user accessible device to provide data relating to a claim for critical illness benefit, the data relating to a current critical illness claim comprising data indicative of the insured and a medical diagnosis of the insured; receiving at an administrative system device data relating to the current critical illness claim, the administrative system device in communication with a data storage device storing data indicative of: first and second categories of medical diagnoses; a plurality of diagnoses associated with the first category and a plurality of diagnoses associated with the second category; a first benefit amount associated with a first occurrence; a second benefit amount, lower than the first benefit amount, associated with a second occurrence; associating by the administrative system the first category or the second category with the current critical illness claim; determining by the administrative system whether a benefit amount had previously been paid to the insured in the category associated with the current critical illness claim; responsive to determining that no benefit amount had previously been paid to the insured in the category associated with the current critical illness claim, for a diagnosis in the determined category, providing by the administrative system an output signal having data indicative of a determination to pay the insured the first occurrence value; and responsive to determining that one benefit amount had been paid to the insured in the category associated with the current critical illness claim, providing by the administrative system an output signal having data indicative of a determination to pay the insured the second occurrence value.

In an embodiment, a non-transitory computer-readable medium has processor-executable instructions stored thereon, which instructions, when executed by the processor, cause the processor to: prompt a user at a user accessible device to provide data relating to a claim for critical illness benefit under a group benefit insurance policy issued to a group policyholder to extend coverage to individual insureds, the data relating to a current critical illness claim comprising data indicative of the insured and a medical diagnosis of the insured; receive data relating to the current critical illness claim; access from a data storage device data indicative of one or more of: first and second categories of medical diagnoses; a plurality of diagnoses associated with the first category and a plurality of diagnoses associated with the second category; a first benefit amount associated with a first occurrence; a second benefit amount, lower than the first benefit amount, associated with a second occurrence; associate the first category or the second category with the current critical illness claim; determine whether a benefit amount had previously been paid to the insured in the category associated with the current critical illness claim; responsive to determining that no benefit amount had previously been paid to the insured in the category associated with the current critical illness claim, for a diagnosis in the determined category, provide an output signal having data indicative of a determination to pay the insured the first occurrence value; and responsive to determining that one benefit amount had been paid to the insured in the category associated with the current critical illness claim, provide an output signal having data indicative of a determination to pay the insured the second occurrence value.

DETAILED DESCRIPTION

Figure 1:
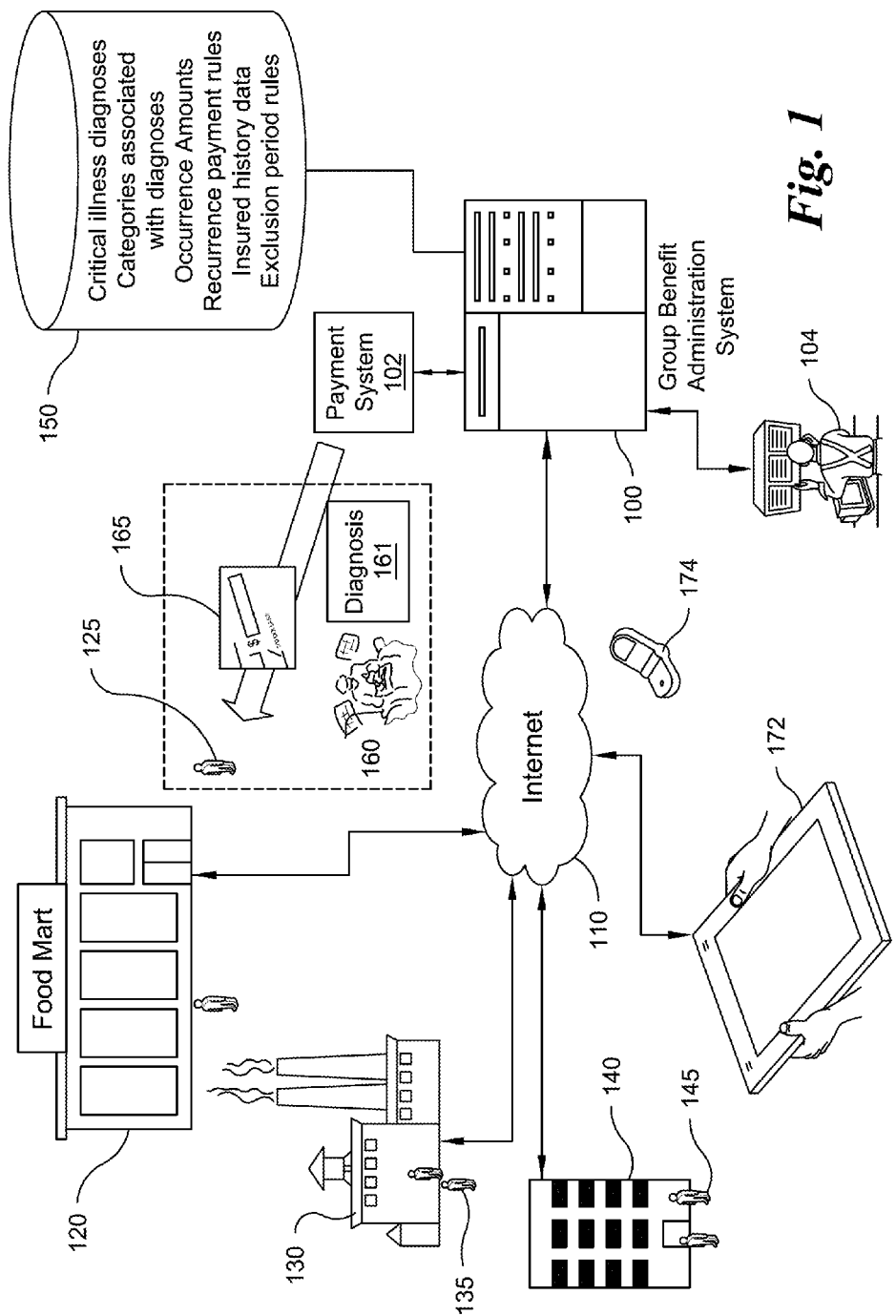
FIG. 1 is a schematic diagram of an exemplary environment for implementation of a method and system of the invention.

It is to be understood that the figures and descriptions of the present invention have been simplified to illustrate elements that are relevant for a clear understanding of the present invention, while eliminating, for the purpose of clarity, many other elements found in typical computer systems and methods for processing of data relating to insurance, including group benefit insurance. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein.

In an embodiment, an insurance company makes available critical care insurance in a group benefits policy. The group benefits policy is issued to a group, such as an employer, a union, an association, a club or other group, for the purpose of extending insurance coverage to individual employees or group members. Individual group members may have their coverage provided automatically by the group or employer, may need to opt to select critical care coverage. Group members may be billed directly by the insurance company, or group members may pay via the group, such as by a payroll deduction calculated to be in an amount sufficient to cover premiums and forwarded by the employer to the insurance company. In critical illness insurance coverage, benefits are available based on a diagnosis of any one of particular conditions, each of which is grouped in a number of categories, such as from two to ten categories. Categories may be made up of related diseases or conditions, such as a first category relating to cardiovascular conditions, a second category relating to cancers, and other categories. A first occurrence of a first covered diagnosis requires the insurance company to pay the insured a first payment. The first payment is in an amount specified in the policy for a first occurrence. Upon a second diagnosis covered under the policy, the available benefits depend on whether the second diagnosis is in the same category as the first diagnosis, or in a different category. If the second diagnosis is in the same category, the second diagnosis is considered a recurrence, and the benefit payable is in an amount lower than the amount specified for a first occurrence. If the second diagnosis is in a different category than the first diagnosis, then the insured may collect a payment in the amount specified for a first occurrence.

Under the policy, the availability of a recurrence benefit may be subject to a waiting period. For example, a waiting period of 3 months, 6 months or one year, or the equivalent periods in days, may be required between diagnoses in order for the recurrence benefit to be available.

As a result, an insured may collect the first occurrence amount more than once under the same policy. For example, if the first category includes cardiovascular diagnoses, such as heart attack, stroke and heart transplant, and the second category includes cancer, then both recurrence benefits are paid.

Payments may be single lump sum payments, multiple payments in a specified total amount, or structured in another manner. While first occurrence payment amounts may be the same in each category in a policy in an embodiment, in another embodiment, the first occurrence payment amounts may differ for different categories.

In an embodiment, the policy may provide a single recurrence payment for each insured in each category for a lifetime, or, in another embodiment, may provide two more recurrence payments.

In an embodiment, a benefit may be provided for hospitalization, which may be based on a number of days of hospitalization, such as a per diem amount, or a lump sum amount for a hospital confinement period.

A partial cancer benefit may be independent of a cancer category, and may be a benefit in a lower amount for a cancer of lower severity than the full cancer benefit. In another embodiment, the partial cancer benefit may be a lower benefit in a cancer diagnosis category.

Referring to FIG. 1, an example of an environment in which a method and system according to an embodiment may be implemented is shown. A group benefit insurance computer system 100, which may be operated by an insurance company, is in communication, via Internet 110, with employers 120, 130, 140. Employer 120 is a retail grocery store, and has employees 125, who may include managers, clerical workers, pharmacists, cashiers, stockers, and other grocery employees. Retail grocery store 120 makes group insurance benefits administered by group benefit insurance computer system 100 available to its employees 125. The group insurance policy includes a critical illness benefit 150, which may be selected by employees 125. The premiums for the group insurance benefit are determined by group benefit insurance computer system 100, and may be added to the periodic premium charged to employer 120. For a critical illness benefit that is funded by the employees 125, a deduction may be charged by employer 120 on each payroll, or on selected payrolls, such as every other one of a semi-monthly payroll, and paid to the insurance company.

Similarly, employer 130 is a factory and has employees 135 who may include factory line workers, line managers, clerical staff, warehouse staff, management and other categories of employees. Employer 130 similarly has a group benefit policy administered by group benefit insurance computer system 100, and which includes the critical illness benefit 150 available to employees 135.

Employer 140 is an office employer, such as a service business, and may have employees 145 who have available critical illness benefit 150. Both employers 130 and 140 may require employees to pay all or a portion of the premium for the critical illness benefit, which may be deducted from payrolls and remitted by the employer to the insurance company. The employers 120, 130, 140 may also pay the critical illness benefit premiums in their entirety, or may pay up to a set first occurrence amount, with any additional amounts being paid by the employees through payroll deductions.

In the example shown, employee 125 has been afflicted with a covered critical illness and is receiving medical treatment 160 in response to the covered critical illness. Employee 125 has an applicable critical illness benefit 150, and submits suitable documentation, such as a certification by a physician or other medical professional as to the diagnosis and the date of diagnosis, copies of medical records relating to the diagnosis, and other documentation, by way of example, as required by the terms of the group benefit insurance policy. Upon receipt of documentation, verification of coverage and that the illness is a covered diagnosis, association of one of the three categories with the covered diagnosis, if the claim is the first claim for that insured 125 in the insurance company will attend to a payment 165 to employee 125 in the amount of the first occurrence payment under the applicable policy. If the claim is the second claim for the applicable category, then the amount of payment 165 will be a lower recurrence amount.

Figure 2:
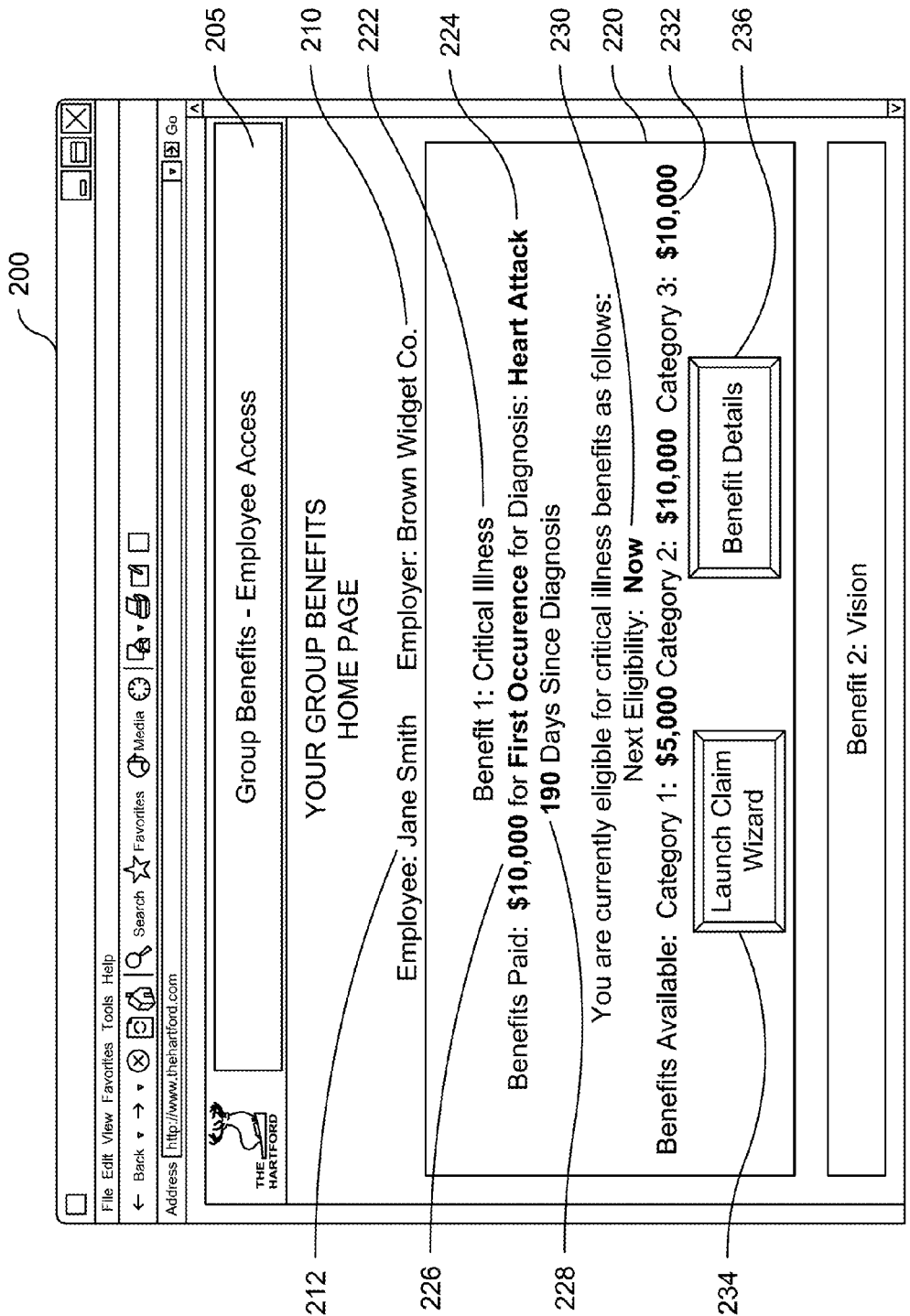
FIG. 2 is an exemplary screen shot on a user-accessible device generated by a system in accordance with an embodiment of the invention for viewing by an insured of coverage information.

Referring to FIG. 2, a screen 200 is shown, generated by a computer system such as computer system 100 of FIG. 1, for an employee covered by a group benefit policy having a critical illness benefit. The screen is labeled to identify the application as group benefits—employee access 205. The system may also permit access to other users, such as employer personnel, such as human resources and benefits personnel, insurance agents and brokers representing an insurance company, and insurance company personnel. A suitably authenticated user employee has accessed the system, which has, responsive to the user log in, accessed data from one or more databases associated with a user identification, and has formatted and served to a user-accessible device, such as a desktop, laptop or tablet computer, a smartphone, a personal digital assistant, by way of example, the screen 200. The employer 210 and employee 212 data have been accessed from databases and are displayed. Benefits that the employee has are each displayed in blocks, such as block 220 displaying data related to a critical illness benefit. Other benefits, such as vision, dental, group life, short term disability, long-term disability, by way of example, may be shown separately, and a portion of a vision benefit block is shown at the bottom of the screen by way of example. Critical illness benefit 222 is shown with data particular to the identified employee, Jane Smith of employer Brown Widget Co., listed. The accessed and displayed data includes benefit paid data, including diagnosis 224, type of benefit (e.g., first occurrence, recurrence, or other category); amount paid 226, and amount of time since diagnosis 228. The amount of time since diagnosis 228 is relevant for the determination of whether the employee is currently eligible for the benefit, or if one or more waiting periods or benefit suspension periods, which may be applicable to all benefits for the insured or to the particular category of the last payment, subsequent to a diagnosis of a covered benefit, is currently in effect. The benefit suspension period may commence on various triggers, depending on policy provisions, such as date of diagnosis as shown in certification by a healthcare professional, date of payment, date of submission of certification of diagnosis, date of company approval of claim, or another applicable date. In this display, the system has accessed date information and applicable rules information, and has determined that the employee is eligible now 230 for benefits. The system may determine and display that the employee is eligible in a given number of days for benefits, or may display different applicable periods for different benefits, e.g., a period of days for eligibility in category 1, and that the insured is eligible now in categories 2 and 3.

Available benefit amounts are listed by category 232. As a first occurrence benefit has been paid in category 1, the system has accessed rules and determined that a recurrence benefit with an available benefit amount of $5,000 is available upon submission of a claim for a covered diagnosis in category 1. In category 2 and category 3, a benefit of $10,000, which is the first occurrence benefit, is available, as determined by a system in accordance with applicable rules upon submission of an acceptable claim for a covered diagnosis in categories 2 or 3. The system may be configured, responsive to user selection of the "Launch Claim Wizard" button 234, to display one or more screens with prompts for a user to provide data for submission of a claim, such as type of diagnosis, date of diagnosis, treatments performed, treating physician identification information, and for submission of electronic certifications by physicians or other medical professionals, electronic medical records, images of paper medical records and certifications, and other documentation that may be required by system rules in order to submit a complete and documented claim for the critical illness benefit. The system may be configured, responsive to user selection of the "Benefit Details" button 236, to provide additional data regarding benefits available for the particular employee user.

Figure 3:
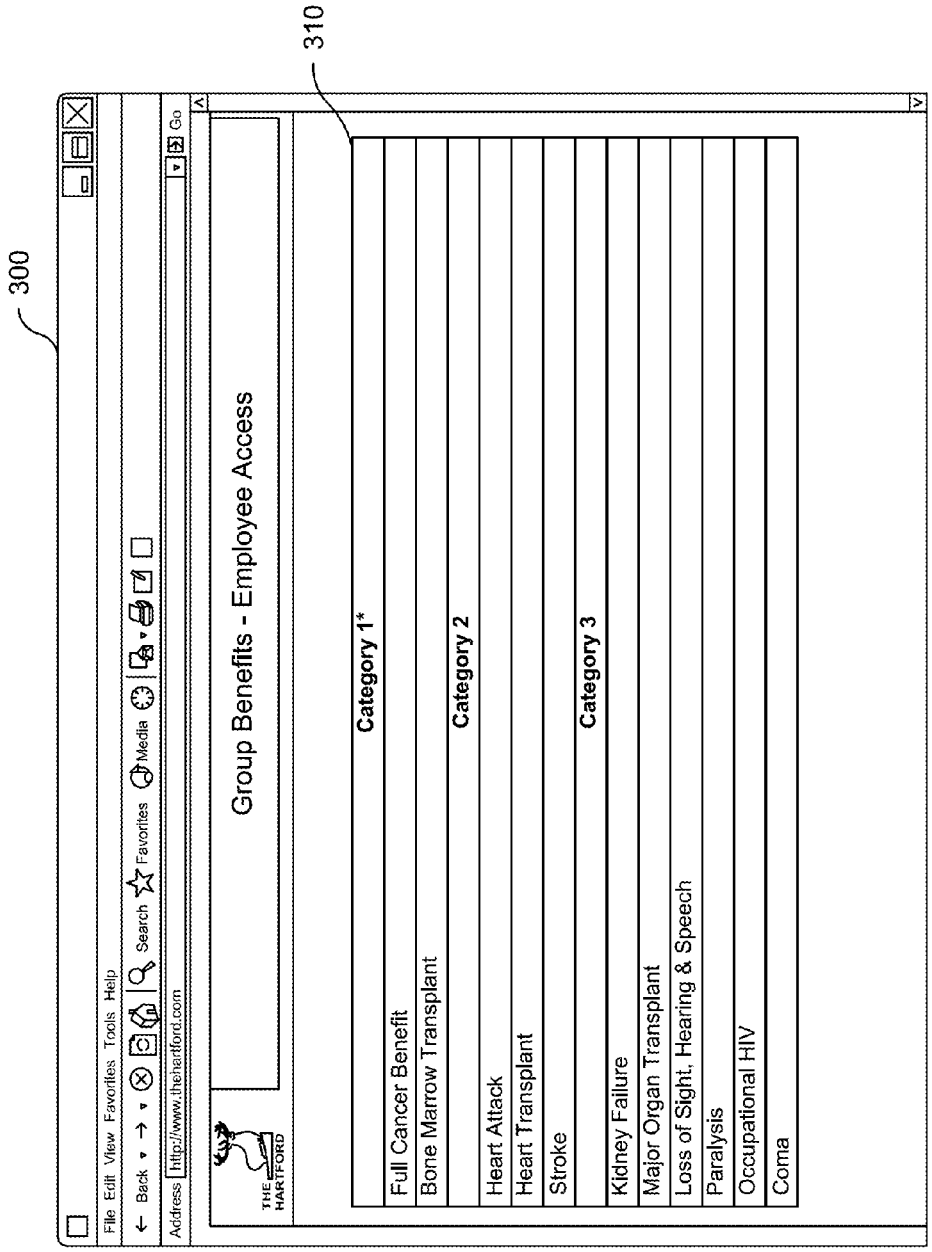
FIG. 3 is an exemplary screen shot on a user-accessible device generated by a system in accordance with an embodiment of the invention, identifying covered conditions and associated categories.

For example, referring to FIG. 3, a system has generated screen 300 on a user-accessible device, including a table 310 showing diagnoses and associated categories, as an example of benefit details that may be displayed. A first category may include certain cancers, having a full benefit, and procedures used in treatment of cancers, such as, here, a bone marrow transplant, employed in treating leukemia. A second category may include cardiovascular conditions, such as heart attack, heart transplant and stroke. The term diagnosis or medical diagnosis used herein includes procedures, such as heart transplant, major organ transplant, coronary artery bypass and other procedures. A third category may include a variety of other serious medical diagnoses, such as major organ transplant, kidney failure, loss of sight, hearing and speech, paralysis, occupational HIV, and coma. The three categories listed are merely exemplary, and the number of categories may be 2 in an embodiment, and may be more than three in other embodiments.

Figure 4:
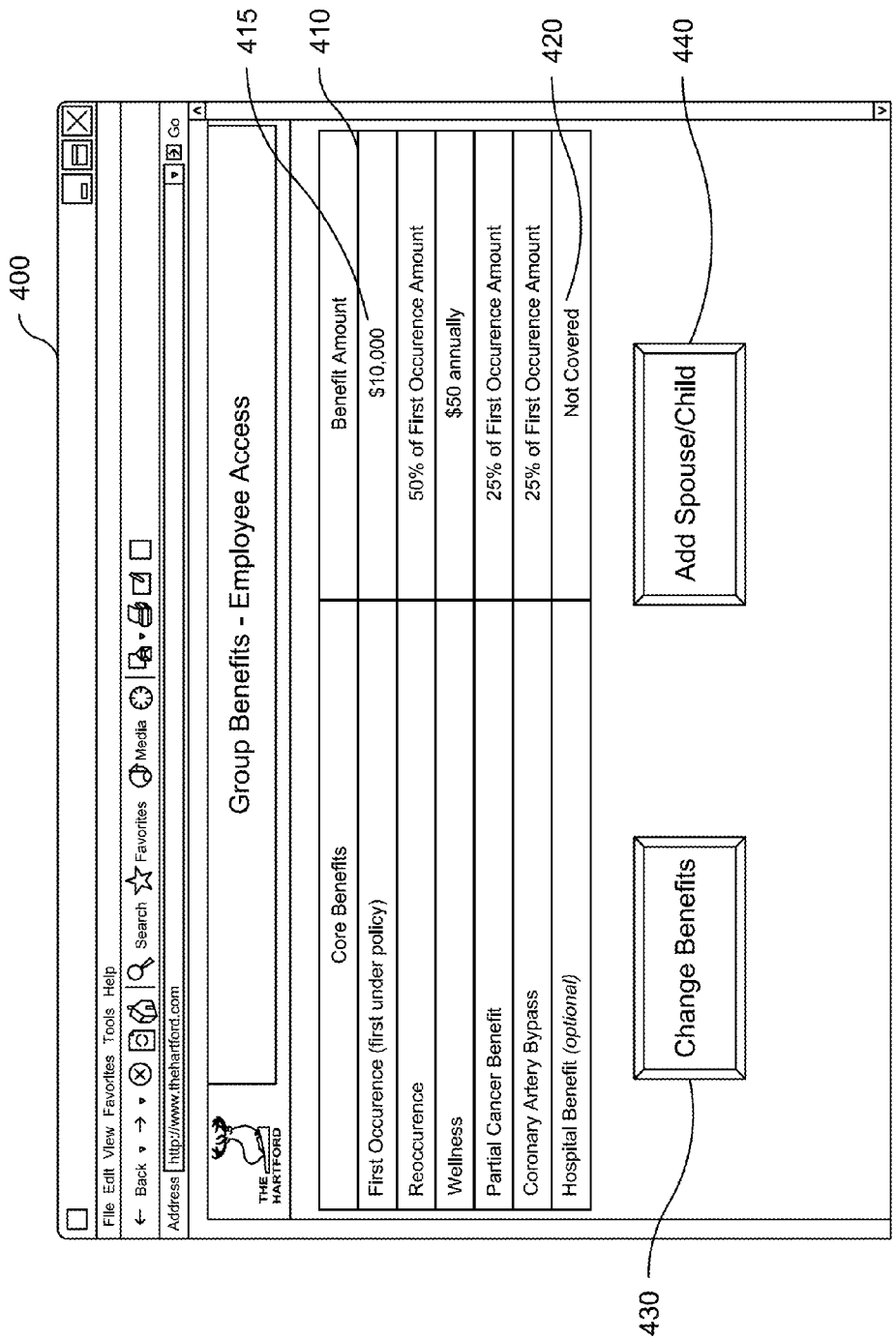
FIG. 4 is an exemplary screen shot on a user-accessible device generated by a system in accordance with an embodiment of the invention for viewing by an insured of coverage information.

Referring to FIG. 4, the system has generated screen 400 for display on a user-accessible device, including a table 410 of the particular employee's benefits. Table 410 includes the employee selected first occurrence amount 415 and the employee selection of no hospital benefits 420. The recurrence benefit, for a second diagnosis in a category, is a percentage of the first occurrence benefit in this policy, and in this case 50%. The percentage may be preset for the policy as a whole, or may be selected. The table 410 further displays data relating to two types of benefits involving lower payment amounts than a recurrence benefit, namely a partial cancer benefit and a coronary artery bypass, both of which pay a single benefit at a lower amount, in this case 25% of the first occurrence amount. These benefits lack a recurrence benefit, and are thus a single payment for the individual for the life of the policy.

The screen 400 also displays an amount of a wellness benefit. A wellness benefit may operate as a reward to an insured for having certain screening or other examinations or tests conducted, or vaccinations obtained. Such tests may include, by way of example, a) bone marrow testing; b) CA15-e (Cancer antigen 15-3 blood test for breast Cancer); c) CA125 (Cancer antigen 125 blood test for ovarian Cancer); d) CEA (carcinoembryonic antigen blood test for colon Cancer); e) Chest x-ray; f) Colonoscopy; g) Flexible sigmoidoscopy; h) Hemocult stool analysis; i) Mammography; including Breast Ultrasound; j) Pap smear; including Thin Prep Pap Test ; k) PSA (prostate specific antigen blood test for prostate Cancer); I) Serum Protein Electrophoresis (test for myeloma); m) Biopsy for skin cancer; n) Blood test for triglycerides; o) HPV (Human Papillomavirus) Vaccination; p) Lipid Panel (total cholesterol count); q) Doppler screening for carotids; r) Doppler screening for peripheral vascular disease; s) Themography; t) Echocardiogram; u) Ultrasound screening of the abdominal aorta for abdominal aortic aneurysms; v) EKG; w) Stress test on bike or treadmill; x) Fasting blood glucose test; and y) Serum cholesterol to determine level of HDL and LDL.

The system displays a change benefit button 430 and an add spouse/child button 440. A change benefit button 430 may cause the system to prompt for changes to the first occurrence amount and other benefits. In an embodiment, the employee may be able to select a first occurrence amount up to a certain amount based on guaranteed issue, i.e., with no proof of insurability. The value may be between $10,000 and $100,000, for example. Coverage between that value and a maximum may be subject to simplified issue rules, such as minimal underwriting. By way of example, the simplified issue rules may provide that the user is presented with a series of questions regarding health conditions. By way of example, the questions may inquire as to whether the user has been diagnosed with or treated for any of certain conditions or diagnoses, either at any time, or during a period, such as one year or two years, prior to the application. The system may require a certification by a treating physician, which may be in electronic or paper form, as to whether the insured has been diagnosed with or treated for specific diseases and conditions. The system may be configured to review the input responses and to notify a user in real time if the requirements for issue have been met. In an embodiment, the limit for guaranteed issue may be age-dependent. For example, a first occurrence amount of up to $50,000 may be available with guaranteed issue for an insured up to age 50 only, and up to only $5000 for insureds of age 50 and above.

A benefit suspension period or waiting period may be implemented, and may have varying terms depending on whether successive diagnoses are within a category or in different categories. For example, a longer benefit suspension period may be provided for diagnoses within a same category, such as two years, while a shorter period, such as 6 months or 180 days, may be provided for diagnoses in different categories.

An add spouse/child function may be implemented responsive to user selection of the add spouse/child button. Coverage of an employee or other group member may be a condition of the addition of a spouse or child. The applicable guaranteed issue limits and simplified issue limits may be the same as the employee or other group member limits, or may be lower for spouses and children.

In an embodiment, group life insurance benefits and critical illness benefits in accordance with an embodiment may be furnished to the same insured with linked conditions. For example, an insured may be able to obtain a premium less than the sum of life coverage and critical illness coverage separately if critical illness payments are deducted from the death benefit amount for the life coverage, or if another amount is deducted from the life coverage responsive to payment of the critical illness benefit. The benefit suspension periods may be shorter if the critical illness benefits are deducted from the death benefit amount under the life coverage.

In an embodiment, a group benefit life insurance policy may include an account value, in which all or a portion of the premium is employed to establish an account value. The insurance policy may be in the form of a deferred annuity, in which premiums increment the account value, and the account value may also increase based on interest credited by an insurance company, in a fixed annuity model, or based on investments selected by the insured, in a variable insurance model. The deferred annuity may be subject to surrender charges for withdrawals prior to a period of years after payment of a premium. A critical illness benefit may include a waiver of surrender charges upon submission of a covered diagnosis. The waiver of surrender charges may be applicable even if no critical illness benefit payment is available, such as for a third occurrence within a category, in a policy which provides a first occurrence and a single recurrence. Similarly, if a life insurance policy has a cash value, surrender of the cash value without surrender charges, waiver of premium benefits, and other benefits may be provided in association with a critical illness benefit.

Other definitions of critical illness may also be available under a policy. For example, the definition of chronic illness of an individual being unable to perform a certain number, e.g., two or three, of activities of daily living (ADLs) without substantial assistance from another individual, or a cognitive impairment such that the individual requires substantial assistance to avoid harm to the individual or to others, may be deemed a critical illness.

Figure 5:
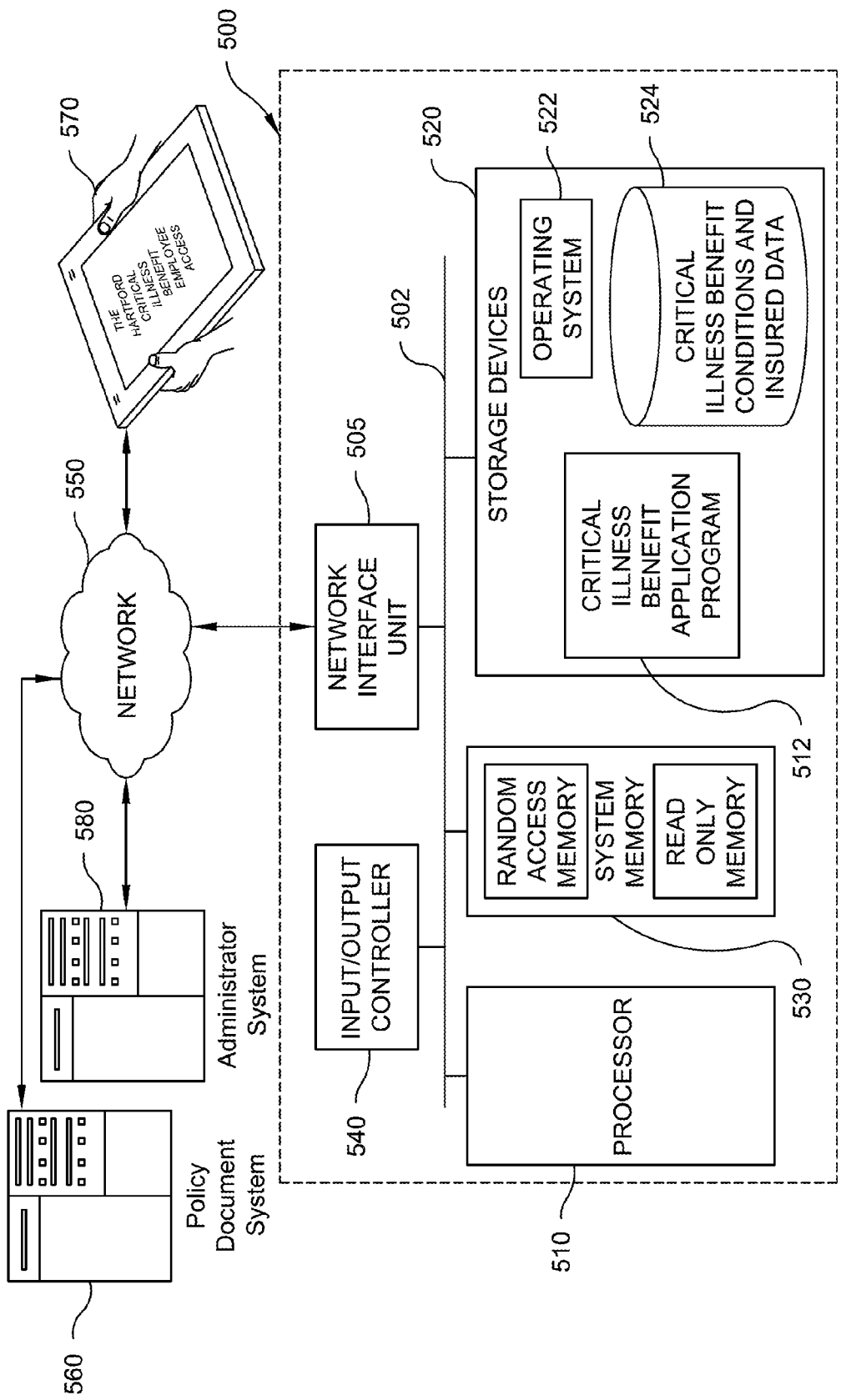
FIG. 5 is a schematic diagram of an exemplary computer system and networked devices in an embodiment of the invention.

Referring to FIG. 5, an exemplary computer system 500 for use in an implementation of the invention will now be described. In computer system 500, processor 510 executes instructions contained in programs such as critical illness benefit application program 512, stored in storage devices 520. Storage devices 520 may include suitable media, such as optical or magnetic disks, fixed disks with magnetic storage (hard drives), tapes accessed by tape drives, and other storage media. Processor 510 communicates, such as through bus 502 and/or other data channels, with network interface unit 505, system memory 530, storage devices 520 and input/output controller 525. Via input/output controller 525, processor 510 may receive data from user inputs such as pointing devices, touch screens, audio inputs and keyboards, and may provide data to outputs, such as data to video drivers for formatting on displays, and data to audio devices. Storage devices 520 are configured to exchange data with processor 510, and may store programs containing processor-executable instructions, and values of variables for use by such programs. Processor 510 is configured to access data from storage devices 520, which may include connecting to storage devices 520 and obtain data or read data from the storage devices, or place data into the storage devices. Storage devices 520 may include local and network accessible mass storage devices. Storage devices 520 may include media for storing operating system 522 and mass storage devices such as critical illness benefit and insured data storage 524 for storing data related to formulas and values of employed in generating illustrations. Such data may include data regarding policies, available recurrence benefits, associations between diagnoses and categories, rules and limits for guaranteed issue and simplified issue, requirements for claims, particular benefit levels associated with particular insureds, claims submitted and paid or denied for insureds, premium rates based on benefit amounts, and other relevant data. In an embodiment, inputs may include user interfaces, including workstations having keyboards, touch screens, pointing devices such as mice, or other user input devices, connected via networked communications to processor 510. Network interface unit 505 may communicate via network 550 with other insurance company computer systems, computer systems of brokers, financial advisors, insureds and owners, remote sources of data, and with systems for implementing instructions output by processor 510. Network 550 may be or include wired or wireless local area networks and wide area networks, and over communications between networks, including over the Internet. Any suitable data and communication protocols may be employed.

Policy document system 560 connected to system 500 via network 550 is configured to receive data applicable to policies, including selected coverage amounts, decisions on claims, correspondence and reports relating to claims, and to generate insurance documents for issue and modification of policies and notification to groups and insureds relating to policies, such as benefit changes, premium bills, cancellation notices, renewal notices, policy changes, approval and denial of claims, and other documents. Policy document system 560 may be configured to generate documents, including policy contracts, certificates and correspondence, from stored templates of documents, populated with data, consistent with policy data and insured data stored in data storage 524. Policy document system 560 may be configured to generate certificates and other documents to notify individual insureds and groups of coverage. Policy document system 560 may generate policy documents and effect delivery of policy documents by accomplishing delivery to user-accessible devices, such as tablet computer 570. Tablet computer 570 displays a message advising a user that a critical illness benefit employee access portal has been reached. Responsive to user submission of suitable credentials, policy document system 560 may make available to tablet computer 570 policy documents for viewing by an authenticated user, such as an employee. Policy document system 560 may also generate documents for printing and physical delivery by postal mail to insureds, as well as generating image files for posting to web servers or for access from user accessible devices, such as tablet computer 570.

Administrator system 580 is a computer system to permit an administrator, such as insurance company personnel, to make changes to policy document templates, to terms and rules associated with policies, including changes to data items, such as applicable guaranteed issue limits for an employer as a whole, in data storage 524, and is in communication, via network 550, with systems 500 and 560.

Figure 6:
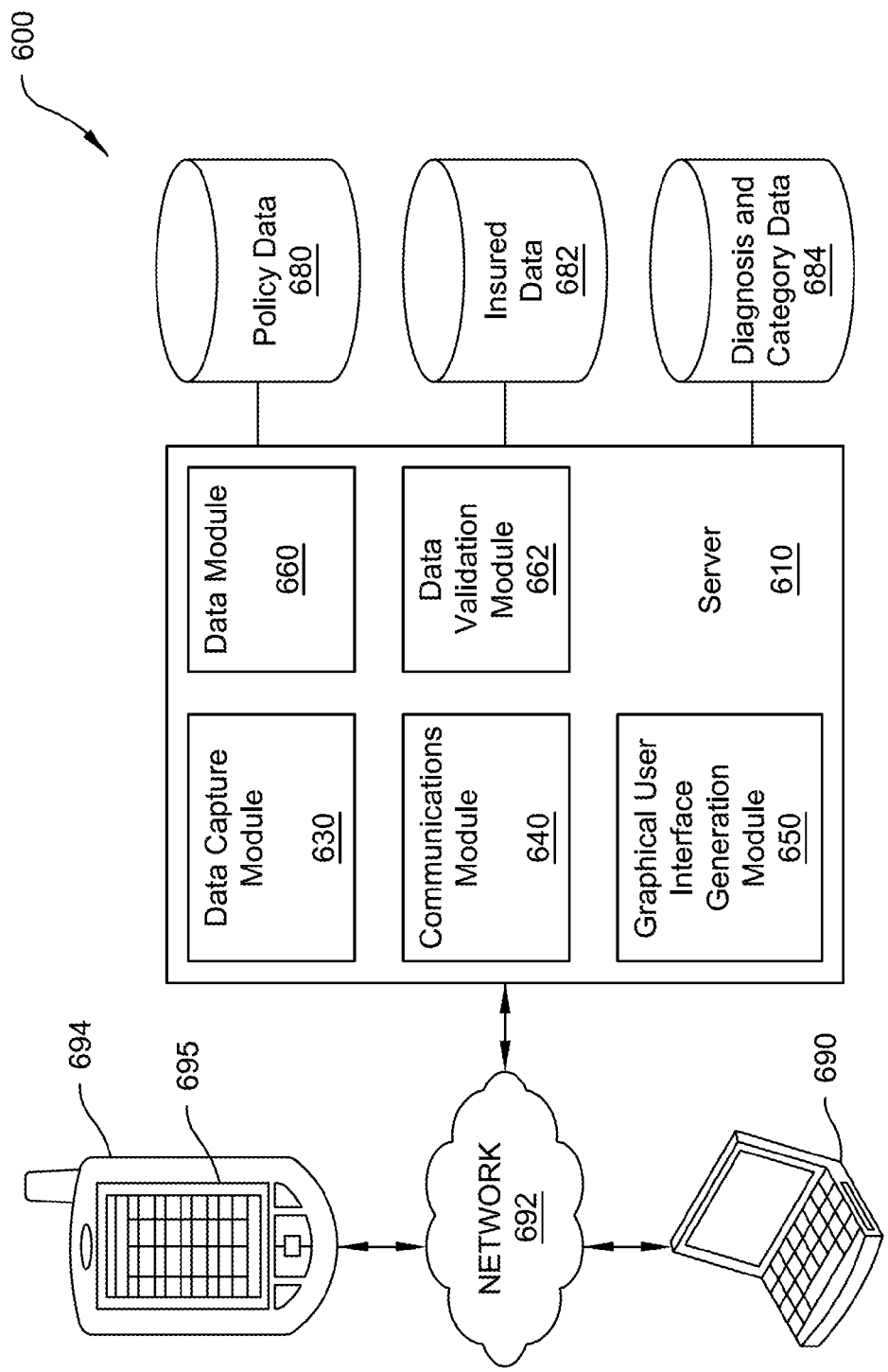
FIG. 6 is a schematic diagram of an exemplary server and associated networked devices in an embodiment of the invention.

Referring now to FIG. 6, another exemplary embodiment of a system 600 for use in an implementation of the present invention is shown. System 600 includes an insurance company server 610 which includes one or more engines or modules which may be utilized to perform one or more steps or functions of the present invention. In an embodiment, the present invention is implemented as one or more modules of a computer software program in combination with one or more components of hardware. In a system for administering group benefit critical illness coverage, such software programs will be used generally where an insured, an employee or other individual who is eligible for insurance, an employer representative, or an insurance agent or broker, has sent a request for data or information to a server and comprises part of the processing done on the server side of the network. In a system for administration of benefits, such software programs will be used, for example, when an insured requests critical illness coverage, a change in coverage, submits a claim, seeks to review current coverage available or status of claim processing, and where an employer or other groups wishes to review available benefits and policy conditions or change policy coverage, such as guaranteed issue first occurrence amounts. The program may be used in an Internet environment, where the server is a Web server and the request is formatted using HTTP (or HTTPS). Alternatively, the server may be in a corporate intranet, and extranet, or any other type of network. Use of the term "Internet" herein, when discussing processing associated with the user's request, includes these other network environments, unless otherwise stated. Additionally, a graphical user interface or insurance processing module may be implemented as an intelligent hardware component incorporating circuitry comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like. One or more functions of a web client or other module may be implemented as application software in the form of a set of processor-executable instructions stored in a memory of a client device, such as smart phone 694 or laptop computer 690, and capable of being accessed and executed by a processor of the client device.

Referring still to FIG. 6, server 610 includes a data capture or input/output module 630, a communications module 640, a dynamic display generation or graphical user interface module 650, a data module 660, and a data validation module 662. Data module 660 is in further communication with a number of databases such as insurance policy database 680, insured database 682 and diagnosis and category data 684. Databases in communication with server 610 may include both internal and/or external/third party databases. By way of example, external databases may include databases of brokers or others having information relating to insureds and applicants for coverage (e.g., spouses and children), such as names and ages. External databases may include databases used for simplified issue underwriting, such as databases of drug prescriptions written for an employee, spouse or child, social media (which may be searched for key words indicative of pre-existing conditions, such as "chemo" or "rehab") and the like. Server 610 may be configured for bulk upload of data for use in administration of insurance policies, such as data relating to employees who are to be automatically covered, from an employer's database or file. One or more modules may be configured to perform data validation steps prior to storing bulk uploaded data. Server 610 may further be configured to permit bulk download of data, such as policy data, data relating to coverage of employees, and benefit data, to a client device, such as to an employer device.

In operation, server 610 is in communication with client devices, such as computer 690 or smart phone 694, via a network which facilitates interaction with server 610 through one or more graphical user interfaces as shown and described herein. As used herein, devices, such as client devices 690, 694 may exchange information via any communication network, such as a Local Area Network (LAN), a Metropolitan Area Network (MAN), a Wide Area Network (WAN), a proprietary network, a Public Switched Telephone Network (PSTN), a Wireless Application Protocol (WAP) network, a Bluetooth network, a wireless LAN network, and/or an Internet Protocol (IP) network such as the Internet, an intranet, or an extranet. Note that any devices described herein may communicate via one or more such communication networks.

Referring still to FIG. 6, utilizing client devices 690, 694, a properly authenticated system user, such as an employee of a covered group or an employer benefits administrator, may request data as to current coverage, changes in coverage, and other data. A properly authenticated system user may provide data to a critical illness benefit administration system to request an increase or decrease in benefit amounts, submit a claim, or make other changes to a policy. A properly authenticated system user in an administrative capacity may also access data and formulas and, for example, add or delete diagnoses, change categories applicable to diagnoses, change formulas for calculating recurrence benefits based on first occurrence amounts, and otherwise change rules and values in view of changes to policies. Policy-related documents, such as certificates, correspondence as to coverage and claim processing and other documents may be stored as data. These documents may be maintained in memory as image files, for example, and available for download and viewing on client devices 690, 694 by a properly authenticated user. In embodiments of the present invention, one or more of the above modules, such as graphical user interface module 650, data module 660 and data validation module 662 may also be implemented in combinations of software and hardware for execution by various types of computer processors coupled to such hardware.

As used herein, a module of executable code may, for instance, comprise one or more physical or logical blocks of computer instructions which may, for instance, be organized as an object, procedure, process or function. Nevertheless, the executables of an identified module need not be physically located together, but may comprise separate instructions stored in different locations which, when joined logically together, comprise the module and achieve the stated purpose for the module such as implementing the business rules logic prescribed by the present system. In the present invention a module of executable code may be a compilation of many instructions, and may even be distributed over several different code partitions or segments, among different programs, and across several devices. Similarly, data, including by way of example policy data, insured data, coverage amounts, associations of rules and diagnoses and recurrence rules may be identified and illustrated herein within modules, and may be embodied in any suitable form and organized within any suitable type of data structure. Such data may be collected as a single data set, or may be distributed over different locations including over different storage devices, and may exist, at least partially, merely as electronic signals on a system and/or network as shown and described herein.

Figure 7:
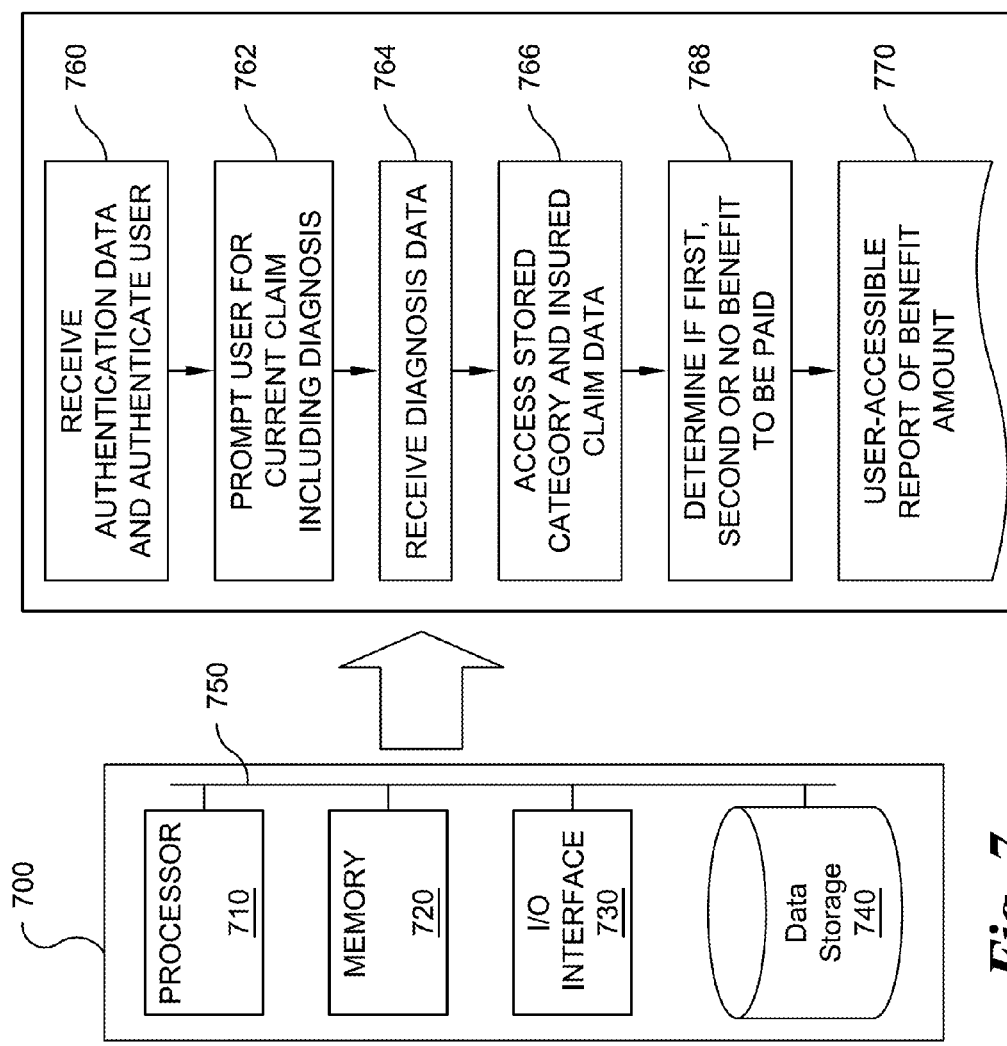
FIG. 7 is a schematic diagram of an exemplary computer server and process flow diagram for implementation of a method and system of the invention.

Referring to FIG. 7, in an embodiment, a computer server or client computer 700 running a client application such as a Web browser or a thick client application renders a graphical user interface, such as one or more screens for displaying current benefits available and prompts for users to change coverages, for viewing and input by users such as insureds and representatives of groups, such as employers, associations, unions and other groups. Server or client computer 700 may include a processor 710, e.g. CPU or multiple processors or multiple core processor, memory 720, I/O interface 730 and a storage mechanism 740 coupled together via a system bus 750 over which the various elements may interchange data and information. Computer 700 implements steps 360-374 in accordance with embodiments of the present invention.

Still referring to FIG. 3, computer 700 receives 760 authentication information from an authorized user, such as an insured employee or human resources representative of agent or broker, employing a user-accessible device, and authenticates the user. The system in this example is configured to receive a claim, and so prompts 762 the user for data and documentation needed for submission of a claim. The system may generate screens to request data from the insured, such as diagnosis, dates, treatments, and documents such as medical reports, and data such as contact information for treating physicians so that the system may direct messages to the physician to provide confirmatory certifications. The system may be configured to communicate with the user via phone user a digital voice response system configured to receive and record data submitted by phone and to instruct the user to submit documents by postal mail, fax, scan and upload or e-mail or other suitable method. The system may be configured to instruct a user to employ a camera of a user-accessible device, such as a smartphone, to provide digital images of medical records and physician certifications, by way of example. The system receives 764 the requested diagnosis data, including documents as needed, from the user-accessible device or via another route, such as a separate submission by postal mail. The system accesses stored category and insured claim data 766, as well as applicable stored rules. The system may determine 768 whether a first occurrence benefit, a second occurrence benefit, no benefit, or a different benefit, such as a wellness benefit or partial cancer benefit, is to be paid, in accordance with applicable rules. The system may generate 770 a user-accessible report of the benefit amount, which may be delivered in any suitable manner, including e-mail, printing and faxing or postal mailing, posting as an image file on a resource accessible to a properly authenticated user, or other manner.

Figure 8:
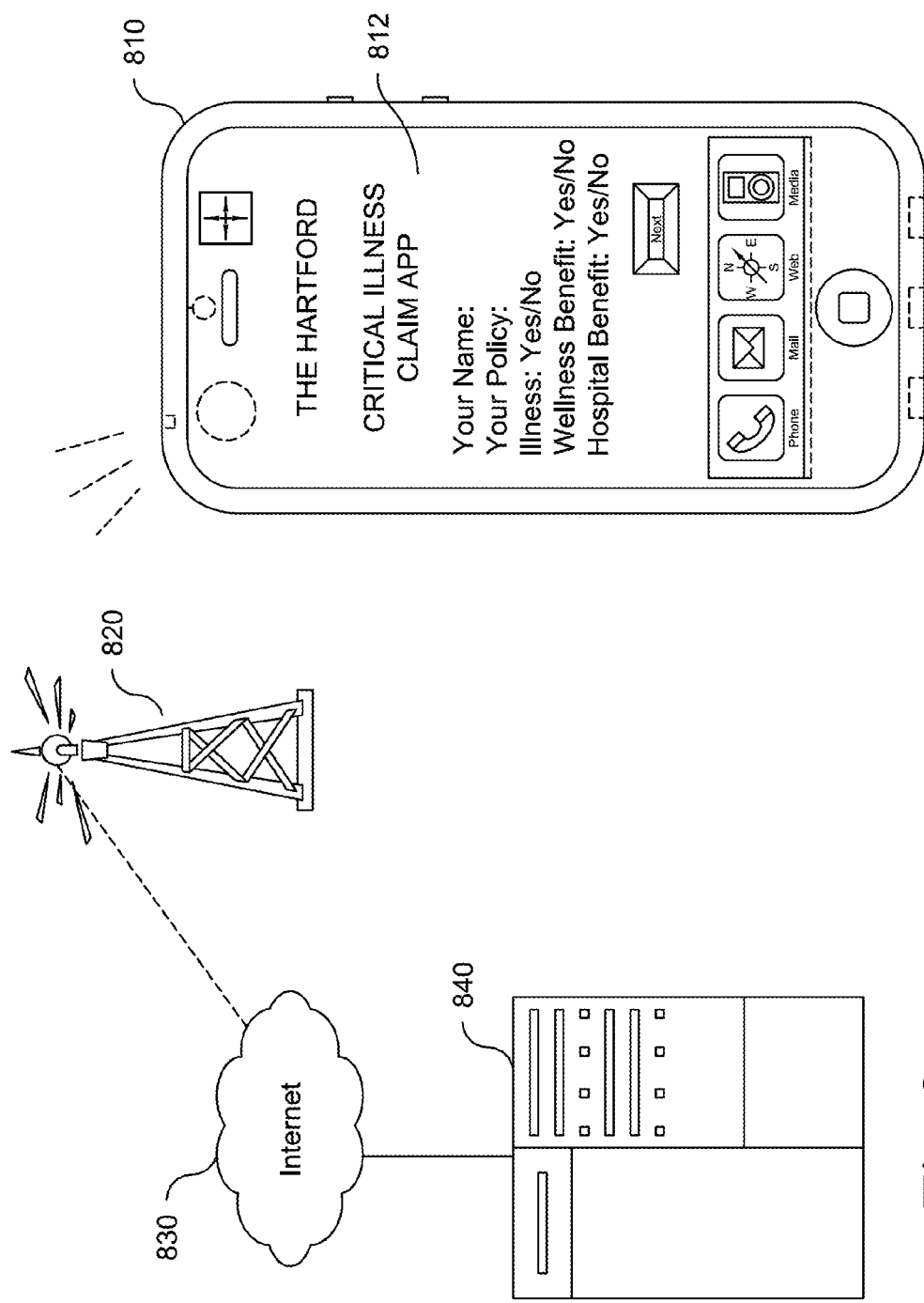
FIG. 8 is a schematic view of an exemplary wireless implementation of a method and system of the invention.
Figure 9:
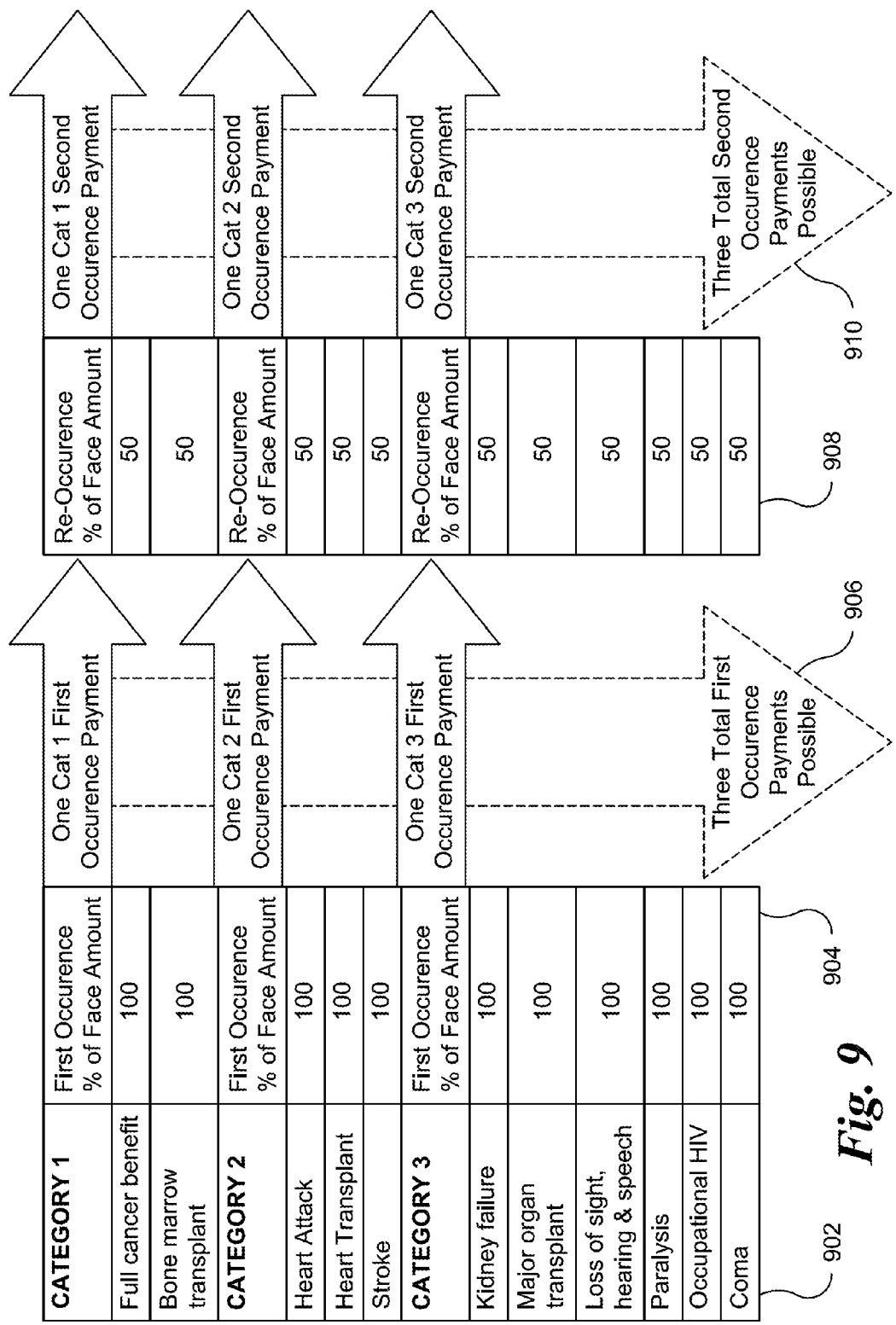
FIG. 9 is a schematic diagram illustrating diagnoses, categories, first and second occurances values and available payments is an embodiment of the invention.

Referring to FIG. 8, a network is illustrated including a wireless device for providing a user interface for submission of claims, review of benefits, changes in benefits, and otherwise accessing data related to critical illness policies. Hardware server 840 is an exemplary computer system, such as an insurance company computer system. Hardware server 840 may include a processor and devices in communication with the processor via a bus, the devices including data storage devices, communications devices, user interfaces, and other devices. Hardware server 840 may be configured, such as through processor-executable instructions stored as program code in one or more of the data storage devices, to provide the functionality of a computer system for processing data related to critical illness benefits, including determination of applicable categories for diagnoses, benefits associated with categories for a particular insured, and generation of reports and instructions for payment of benefits. Hardware server 840 is in communication, via network 830, which may include one or more local area networks, wide area networks and interconnected networks (including the Internet), with a wireless communications network, represented by antenna 820. The wireless communications network may be a wireless telephone communications network for transmission of voice and data to and from mobile wireless devices, such as cellular telephones, smart phones and computers. Handheld wireless communications device 810 is in wireless communication with the wireless communications network via antenna 820. Handheld wireless communications device may be any device capable of bidirectional wireless communications via cellular telephone networks, wi-fi devices, two-way radio, or any other form of wireless communications. Handheld wireless communications device 810 may be a cellular telephone, smart phone, personal digital assistant, tablet computer, notebook computer, or other type of wireless communications device with a display and processing capability. Via handheld wireless communications device 810, a user may submit claims, as indicated in the illustrated application screen, change benefits, create and submit images of certifications and other medical records, receive policy documents, including certifications and notifications, receive statements including listings of benefits, applicable wait periods, and other documents.

In an embodiment, handheld wireless communications device 810 may include a processor and memory device or memory devices in communication with the processor, as well as wireless antenna assemblies and one or more displays, such as touch screen displays, in communication with the processor. In an embodiment, a memory device of handheld wireless communications device 810 has stored therein an application program including processor executable instructions for prompting a user to provide authentication information, wellness procedure, hospitalization information, diagnosis information, access stored data relating to past claims and benefits, and indicate whether a claim is approvable or not. The application program may generate display 812 to prompt the user to select a type of claim, and further displays to prompt the input of particular data. The application program may retrieve coverage and other data via server 840 and may display claim processing results Any steps described in the present application as being performed by a server-based or other insurance company computer system, by way of example, may be performed, in whole or in part, by a processor of a handheld device executing instructions stored in a non-transitory computer-readable medium of the handheld device.

Communications to insureds and groups may be dispatched in any suitable manner. By way of example, a printing and mailing system may print on paper and dispatch by postal mail a statement or letter enclosing a certificate or a decision on a claim, or other data. The communication may be provided as data for display on a wireless device, such as handheld wireless communications device 810 of FIG. 8.

A processor may provide the central processing unit (CPU) functions of a computing device on one or more integrated circuits. The term "processor" may include multi-core processors and central processing units including multiple microprocessors.

In embodiments, a processor may provide an output signal having data indicative of one or more data items. An output signal may be carried either over a suitable medium, such as wire or fiber, or wirelessly. An output signal may transmit data from one device to another directly, such as over a bus of a computer system from a processor to a memory device, or indirectly, such as over multiple networks, and with intermediate steps of storage in a buffer or memory device and retransmission. Such an output signal may be provided by the processor to a bus of a computer system together with address data at a series of clock intervals. The address data may designate a destination device on a bus, by way of example. In embodiments, an output signal may be a signal output from a hardware communications device of a computer system to a network, such as a local area network, a wide area network, or a network of interconnected networks, such as the Internet. Output signals may include, by way of example, data identifying formats, fields, and content of fields. Signals may be compatible with any appropriate format. For example, data may be formatted in accordance with a data format for insurance data, such as an ACORD compatible format. Reference to an output signal having particular data may include one or more signals bearing the information. Multiple signals bearing the information may include sequences of digital data bearing the information interleaved with sequences of digital data relating to other information. By way of example, a signal may be packetized for transmission. By way of further example, an output signal may take the form of an uncompressed digital signal or a compressed digital signal.

A system on which the methods of embodiments of the present invention may be implemented includes at least one central processing computer or computer network server. Network server includes at least one controller or central processing unit (CPU or processor), at least one communication port or hub, at least one random access memory (RAM), at least one read-only memory (ROM) and one or more databases or data storage devices. All of these later elements are in communication with the CPU to facilitate the operation of the network server. The network server may be configured in many different ways. For example, network server may be a conventional standalone server computer or alternatively, the function of server may be distributed across multiple computing systems and architectures.

Network server may also be configured in a distributed architecture, wherein databases and processors are housed in separate units or locations. Some such servers perform primary processing functions and contain at a minimum, a RAM, a ROM, and a general controller or processor. In such an embodiment, each of these servers is attached to a communications hub or port that serves as a primary communication link with other servers, client or user computers and other related devices. The communications hub or port may have minimal processing capability itself, serving primarily as a communications router. A variety of communications protocols may be part of the system, including but not limited to: Ethernet, SAP, SAS™, ATP, Bluetooth, GSM and TCP/IP.

Data storage device may include a hard magnetic disk drive, optical storage units, CD-ROM drives, or flash memory. Data storage devices contain databases used in processing transactions and/or calculations in accordance with embodiments of the present invention, including databases of diagnosis, occurrence amount, insured and other data. In one embodiment, database software creates and manages these databases. Insurance related calculations and/or algorithms in accordance with an embodiment of the present invention are stored in storage device and executed by the CPU.

The controller comprises a processor, such as one or more conventional microprocessors and one or more supplementary co-processors such as math co-processors. The processor is in communication with a communication port through which the processor communicates with other devices such as other servers, user terminals or devices. The communication port may include multiple communication channels for simultaneous communication with, for example, other processors, servers or client terminals. As stated, devices in communication with each other need not be continually transmitting to each other. On the contrary, such devices need only transmit to each other as necessary, may actually refrain from exchanging data most of the time, and may require several steps to be performed to establish a communication link between the devices.

The processor also is in communication with a data storage device. The data storage device may comprise an appropriate combination of magnetic, optical and/or semiconductor memory, and may include, for example, RAM, ROM, flash drive, an optical disc such as a compact disc and/or a hard disk or drive. The processor and the data storage device each may be, for example, located entirely within a single computer or other computing device; or connected to each other by a communication medium, such as a USB port, serial port cable, a coaxial cable, an Ethernet type cable, a telephone line, a radio frequency transceiver or other similar wireless or wireline medium or combination of the foregoing.

The data storage device may store, for example, (i) a program (e.g., computer program code and/or a computer program product) adapted to or configured to direct the processor in accordance with embodiments of the present invention, and particularly in accordance with the processes described in detail hereinafter with regard to the controller; (ii) a database adapted to store information that may be utilized to store information required by the program. The program may be stored, for example, in a compressed, an uncompiled and/or an encrypted format, and may include computer program code. The instructions of the program may be read into a main memory of the processor from a non-transitory computer-readable medium other than the data storage device, such as from a ROM or from a RAM. While execution of sequences of instructions in the program causes the processor to perform the process steps described herein, hard-wired circuitry may be used in place of, or in combination with, software instructions for implementation of the processes of embodiments of the present invention. Thus, embodiments of the present invention are not limited to any specific combination of hardware and software.

Suitable computer program code may be provided for performing numerous functions such as associating a diagnosis with a category, determining available benefit amounts, applying rules for guaranteed issue, and other calculations. The functions described above are merely exemplary and should not be considered exhaustive of the type of function which may be performed by the computer program code of embodiments of the present inventions.

The computer program code required to implement the above functions (and the other functions described herein) can be developed by a person of ordinary skill in the art, and is not described in detail herein.

A computing system may include modules, which may be implemented in hardware, software, or combinations of software and hardware, operably inter-connected via a bi-directional connection with a central serial bus or other bus. A system may include a display module and a generating module. The generating module is used for generating an insurance product contracts and other documents, which documents are then delivered to owners, insureds, beneficiaries, brokers, advisors and others, via any suitable hard copy or electronic method.

The computing system may be in communication with one or more payment systems for effecting payments to insureds, and to premium billing and collections systems for billing and collecting premiums from groups and individual insureds.

The term "computer-readable medium" as used herein refers to any medium that provides or participates in providing instructions to the processor of the computing device (or any other processor of a device described herein) for execution. Such a medium may take many forms, including but not limited to, non-volatile media, non-transitory media, tangible media, volatile media, and transmission media. Non-volatile media, non-transitory media and tangible media include, for example, optical or magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, a carrier wave as described hereinafter, or any other medium from which a computer can read.

Various forms of computer readable media may be involved in carrying one or more sequences of one or more instructions to the processor (or any other processor of a device described herein) for execution. For example, the instructions may initially be borne on a magnetic disk of a remote computer. The remote computer can load the instructions into its dynamic memory and send the instructions over an Ethernet connection, cable line, or even telephone line using a modem. A communications device local to a computing device (or, e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

Servers of embodiments of the present invention may also interact and/or control one or more user devices or terminals. The user device or terminal may include any one or a combination of a personal computer, a mouse, a keyboard, a computer display, a touch screen, LCD, voice recognition software, or other generally represented by input/output devices required to implement the above functionality. The program also may include program elements such as an operating system, a database management system and "device drivers" that allow the processor to interface with computer peripheral devices (e.g., a video display, a keyboard, a computer mouse, etc).

An exemplary advantage of a method and system of the present invention is that the insureds have an incentive to maintain critical illness coverage after receiving a first benefit, while balancing the risk borne by the insurer, such as by limiting the amount payable for a later similar diagnosis.

While particular embodiments of the invention have been illustrated and described in accordance with administration of insurance policies, various modifications and combinations can be made without departing from the spirit and scope of the invention, and all such modifications, combinations, and equivalents are intended to be covered and claimed.

What is claimed is:

1. A computer system for processing data related to a group benefit insurance policy issued to a group policyholder to extend coverage to individual insureds and having a critical illness benefit, comprising:

a data storage device storing data indicative of: a plurality of categories of medical diagnoses; a plurality of diagnoses associated with each of the categories; a first occurrence value; a second occurrence value; and prior claims under the critical illness benefit by the insured; and a processor in communication with the data storage device, the processor configured to:

receive via a network from a user-accessible device data associated with a current claim for a critical illness benefit, the data including data indicative of an insured and a diagnosis of a medical condition of the insured;

access from the data storage device the data indicative of diagnoses, categories, and prior claims;

determine a category corresponding the diagnosis of the current claim;

determine whether a prior claim had been paid to the insured for a diagnosis in the determined category;

responsive to determining that no prior claim had been paid to the insured for a diagnosis in the determined category, provide an output signal having data indicative of instructions to pay the insured the first occurrence value; and responsive to determining that one and only one prior claim had been paid to the insured for a diagnosis in the determined category, provide an output signal having data indicative of instructions to pay the insured the second occurrence value.

2. The computer system of claim 1, wherein the processor is further configured to provide data indicative of the instructions to the user accessible device.

3. The computer system of claim 1, wherein the first occurrence value is greater than the second occurrence value.

4. The computer system of claim 1, wherein the processor is further configured to, responsive to determining that two prior claims had been paid to the insured for a diagnosis in the determined category, provide an output signal having data indicative that no payment is to be made to the insured.

5. The computer system of claim 1, wherein the processor is further configured to, responsive to receiving via a network from a user-accessible device data indicative of a request for a premium waiver, and responsive to determining that the request states that the insured is prevented from employment as a result of a medical condition, providing an output signal to a premium billing system to implement a waiver of premiums.

6. The computer system of claim 1, wherein the instructions are indicative of payment of the first occurrence value as a lump sum.

7. The computer system of claim 1, wherein the processor is further configured, responsive to receipt of data indicative of health screening services received by the insured, provide an output signal having data indicative of instructions to pay a health screening amount to the insured.

8. The computer system of claim 1, wherein the processor is further configured to, responsive to receipt of the claim, provide an output signal having data indicative of waiver of a surrender charge on an annuity account of the insured.

9. The computer system of claim 1, wherein the processor is further configured to apply differential benefit exclusion periods dependent on the category associated with the current claim.

10. The computer system of claim 1, wherein the processor is further configured to cause the user-accessible device to prompt a user to create an image file of a document.

11. The computer system of claim 1, wherein the processor is further configured to, responsive to receipt of a diagnosis of a cancer in a partial cancer category, provide a signal indicative of a benefit amount lower than a reoccurrence value.

12. A computer-implemented method for processing data related to a group benefit insurance policy issued to a group policyholder to extend coverage to individual insureds and having a critical illness benefit, comprising:

prompting a user at a user accessible device to provide data relating to a claim for critical illness benefit, the data relating to a current critical illness claim comprising data indicative of the insured and a medical diagnosis of the insured;

receiving at an administrative system device data relating to the current critical illness claim, the administrative system device in communication with a data storage device storing data indicative of: first and second categories of medical diagnoses; a plurality of diagnoses associated with the first category and a plurality of diagnoses associated with the second category; a first benefit amount associated with a first occurrence; a second benefit amount, lower than the first benefit amount, associated with a second occurrence;

associating by the administrative system the first category or the second category with the current critical illness claim;

determining by the administrative system whether a benefit amount had previously been paid to the insured in the category associated with the current critical illness claim;

responsive to determining that no benefit amount had previously been paid to the insured in the category associated with the current critical illness claim, for a diagnosis in the determined category, providing by the administrative system an output signal having data indicative of a determination to pay the insured the first occurrence value; and responsive to determining that one benefit amount had been paid to the insured in the category associated with the current critical illness claim, providing by the administrative system an output signal having data indicative of a determination to pay the insured the second occurrence value.

13. The computer-implemented method of claim 12, wherein the medical diagnoses associated with the first category comprise heart attack, heart transplant and stroke.

14. The computer-implemented method of claim 13, wherein the medical diagnoses associated with the second category comprise cancer.

15. The computer-implemented method of claim 14, wherein the data storage device further stores data indicative of a third category of medical diagnosis, the third category of medical diagnosis comprising major organ transplant.

16. The computer-implemented method of claim 12, further comprising, responsive to determining that a benefit amount had been paid in any category, determining whether a waiting period after the payment had expired, and providing an output signal indicative of no benefit payment to be made responsive to determining that the waiting period had not expired.

17. The computer-implemented method of claim 12, further comprising, responsive to a request for a change in coverage, determining whether a requested new benefit amount is guaranteed issue, and responsive to determining that the amount is guaranteed issue, providing an output signal having data indicative of guaranteed issue.

18. A non-transitory computer-readable medium having processor executable instructions stored thereon, which instructions, when executed by the processor, cause the processor to:

prompt a user at a user accessible device to provide data relating to a claim for critical illness benefit under a group benefit insurance policy issued to a group policyholder to extend coverage to individual insureds, the data relating to a current critical illness claim comprising data indicative of the insured and a medical diagnosis of the insured;

receive data relating to the current critical illness claim, access from a data storage device data indicative of one or more of: first and second categories of medical diagnoses; a plurality of diagnoses associated with the first category and a plurality of diagnoses associated with the second category; a first benefit amount associated with a first occurrence; a second benefit amount, lower than the first benefit amount, associated with a second occurrence;

associate the first category or the second category with the current critical illness claim;

determine whether a benefit amount had previously been paid to the insured in the category associated with the current critical illness claim;

responsive to determining that no benefit amount had previously been paid to the insured in the category associated with the current critical illness claim, for a diagnosis in the determined category, provide an output signal having data indicative of a determination to pay the insured the first occurrence value; and responsive to determining that one benefit amount had been paid to the insured in the category associated with the current critical illness claim, provide an output signal having data indicative of a determination to pay the insured the second occurrence value.

19. The non-transitory computer-readable medium of claim 18, wherein the instructions, when executed by the processor further cause the processor to provide an output signal to cause the user-accessible device to display a prompt for certification by a licensed medical professional of the diagnosis of the current claim.

20. The non-transitory computer-readable medium of claim 18, wherein the instructions, when executed by the processor, further cause the processor, responsive to a determination of a payment, to calculate a reduced amount of a death benefit of associated group life insurance coverage on the life of the insured.

* * * * *